US00PP18495P2

(12) United States Plant Patent
Moon

(10) Patent No.: US PP18,495 P2
(45) Date of Patent: Feb. 19, 2008

(54) OAK TREE NAMED 'QXMTF'

(50) Latin Name: ***Quercus* sp.**
Varietal Denomination: QXMTF

(75) Inventor: Dwayne C. Moon, Walton County, GA (US)

(73) Assignee: Southern Selections, LLC, Loganville, GA (US)

( * ) Notice: Subject to any disclaimer, the term of this patent is extended or adjusted under 35 U.S.C. 154(b) by 0 days.

(21) Appl. No.: 11/443,686

(22) Filed: May 31, 2006

(51) Int. Cl.
*A01H 5/00* (2006.01)

(52) U.S. Cl. ..... Plt./225

(58) Field of Classification Search ..... Plt./225
See application file for complete search history.

*Primary Examiner*—Kent Bell
*Assistant Examiner*—June Hwu
(74) *Attorney, Agent, or Firm*—Polster, Lieder, Woodruff & Lucchesi, LC

(57) ABSTRACT

An oak tree hybrid named 'QXMTF' believed to be a hybrid of Shumard Oak (*Quercus Shumardi*); and Southern Red Oak (*Quercus falcata*) characterized by a dense pyramidal growth habit, unique compact foliage and a consistent orange fall color.

9 Drawing Sheets

Latin name of genus and species: *Quercus* sp.
Varietal denomination: *Quercus* hybrid oak tree which I have named 'QXMTF'.

BACKGROUND OF THE INVENTION

The present invention relates to a new and distinct variety of Oak Tree which is believed to be a *Quercus* hybrid. My new variety has been given the varietal name 'QXMTF'.

Discovery

I discovered my new tree in the spring of 1997 as a chance seedling growing in a cultivated nursery field of *Quercus shumardii* at Moon's Tree Farm, Inc. in Loganville, Walton County, Ga.

The parentage of this tree is unclear. It is definitely a red oak type tree. Representative species include Pin Oak (*Quercus palustris*) or Red Oak (*Quercus rubra*). There are also several related species, including Nuttall Oak (*Quercus nuttalli*), Shumard Oak (*Quercus shumardii*) and Southern Red Oak (*Quercus falcata*). My new tree has characteristics and a history that have prevented making an exact identification. I believe, however, that it is a new hybridization of *Quercus shumardii* and *Quercus falcata.*

Red Oak types readily hybridize with one another, and there is a high probability that this tree is a result of a random cross between a Southern Red Oak and a Shumard Oak. These species of Red Oak overlap one another across much of their range. For example, in the USDA Forest Service native range maps of Shumard Oak and Southern Red Oak, the two species overlap each other in Eastern Texas, Arkansas, Louisiana, Mississippi, Alabama, Georgia, Northern Florida, South Carolina, North Carolina, Tennessee and Southwestern Kentucky. Hybrids are common in these regions and can easily make up a large population of the trees in any given area.

Origin of Tree

My new tree originated in a group of Shumard Oak seedlings purchased from a nursery in Northern Florida in the winter of 1996. These seedlings were planted in a liner field for one year. They were then harvested from the liner production area and replanted in a production field in 1997. It was in this production field that I discovered 'QXMTF'. Evaluation of this tree continued in this field until it was transplanted to an observation area adjacent to the production field in Walton County, Ga. in 2003.

As I observed the original tree of my new variety, the uniqueness of this tree became apparent because of a dense pyramidal growth habit, distinct leaf shape and consistent orange fall color. These characteristics distinguish my new tree from any oaks of which I am aware.

Propagation

In 2002, this original tree of my variety was successfully propagated by vegetative, softwood cuttings at my direction, and the resulting progeny have proven the characteristics of my new variety to be genetically stable. Softwood cuttings three to five inches long were treated with 3000-ppm potassium indole-3-butyric acid (KIBA). The cuttings were then placed in peat pots filled with horticultural growing media and then intermittently misted for a period of five to six weeks.

Uniqueness

My new variety is unique and different from known cultivators in that it has a dense pyramidal growth habit, a distinct leaf shape and consistent orange fall color.

Use

I have observed this tree of my new variety for a period of time and believe it is particularly useful as a specimen or for grouping in lawns, parks, golf courses, commercial landscapes, and as a street tree. It provides good shade, is a relatively fast grower, adapts well to various planting conditions, and has good structural integrity. It also provides interest with its compact foliage that turns orange in the fall.

BRIEF SUMMARY OF THE INVENTION

Industry Representation

Cultivated oaks are generally produced as seedling material. This accounts for a high degree of variability in the industry, both in the landscape and nursery. Recent improvements in technology have enabled the industry to develop oak selections through vegetative propagation. As far as I am aware, my new tree is distinct from seedling and patented selections in that, as a hybrid, it has a dense, pyramidal growth habit, unique compact foliage and a consistent orange fall color.

Background

Typical Shumard Oaks are pyramidal trees with canopies that spread with age. My new tree has an upright pyramidal shape, but I expect the canopy to spread with age as is typical of both *Quercus shumardii* and *Quercus falcata* species. Shumard Oaks typically reach 40 to 60 feet high and 50 to 55 feet wide in the landscape, but can reach 100 feet or more in nature. Southern Red Oaks develop to a height of 70 to 80 feet and a width of 50 to 60 feet, and can exceed 100 feet in height. The ultimate height and width of my new variety is not known.

Fixed Traits

My new variety has been asexually propagated by vegetative cuttings at my direction. Asexual reproduction was accomplished in Walton County, Ga. This propagation and observation of the resulting progeny have proven the characteristics of my new variety to be stable and reproduce true to type. Furthermore, these observations lead me to believe that my new variety represents a new and improved variety of oak tree which appears to be a hybridization of Shumard Oak and Southern Red Oak as evidenced by the dense, pyramidal growth habit, glossy compact foliage and orange fall color.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

Figure 1:
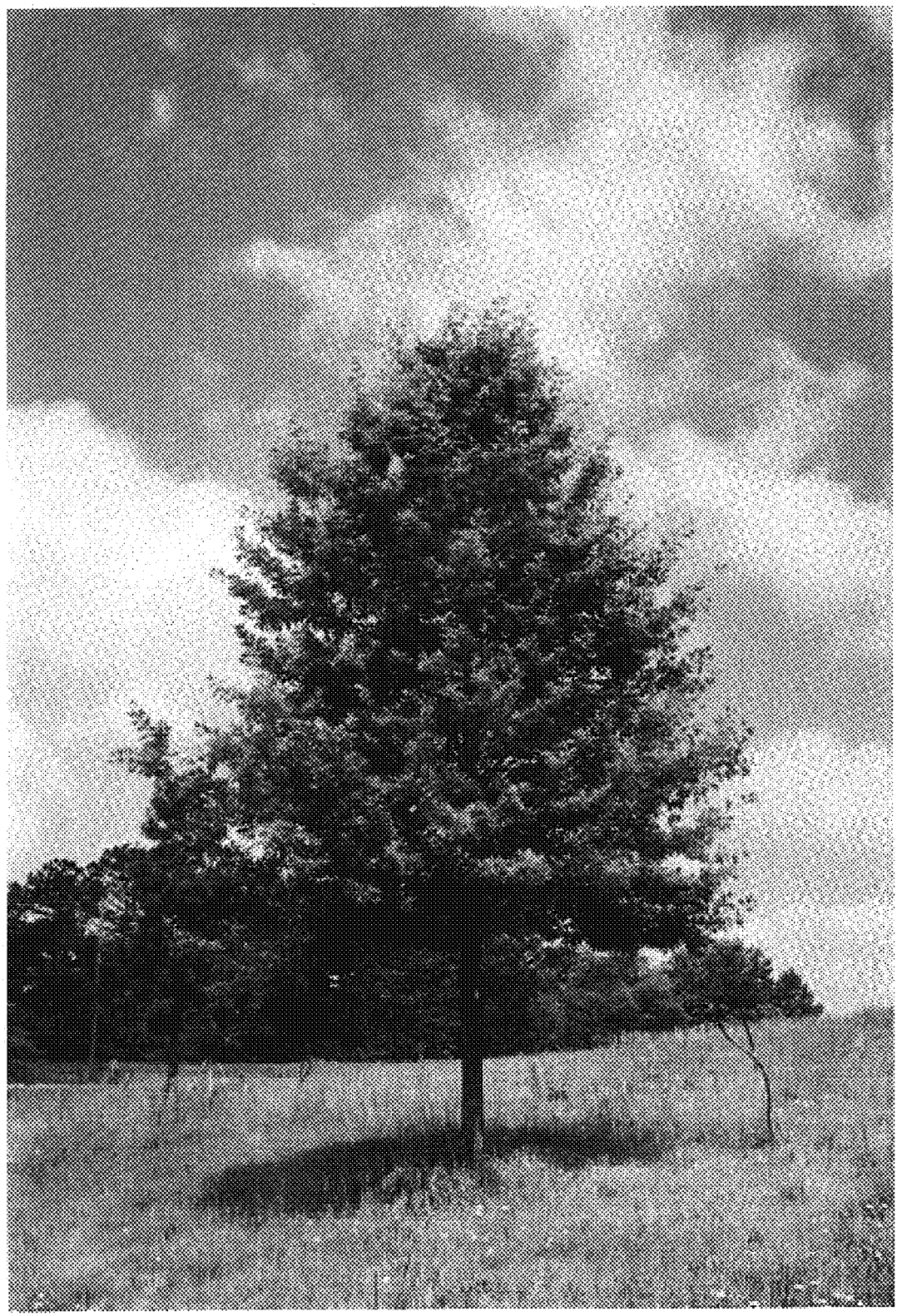
FIG. 1 is a photograph of the original tree of my new variety in summer leaf at nine (9) years of age.
Figure 2:
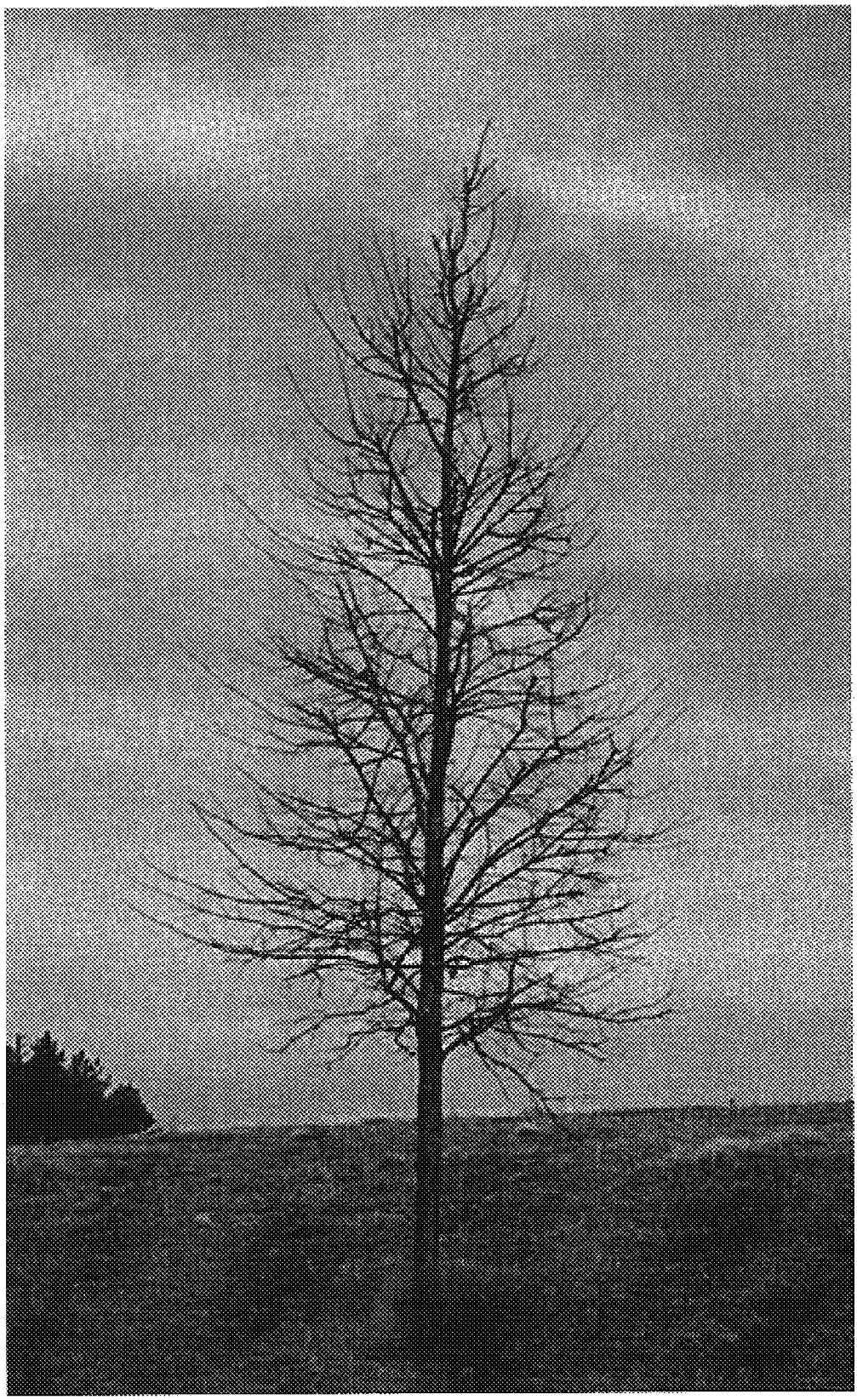
FIG. 2 is a photograph of the original tree of my new variety during winter.
Figure 3:
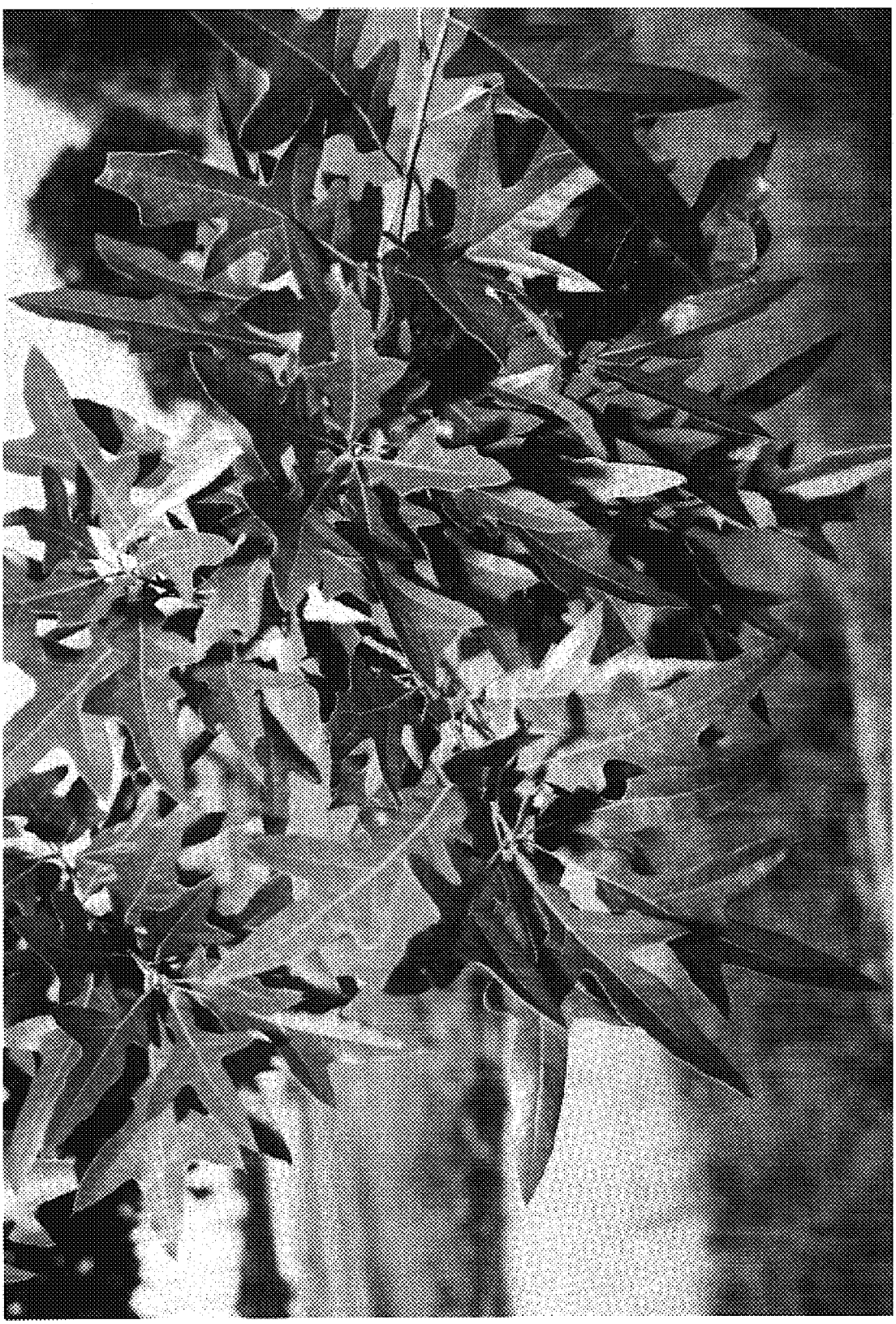
FIG. 3 is a close up of leaves depicting the upper side of summer leaves from a tree of my new variety.
Figure 4:
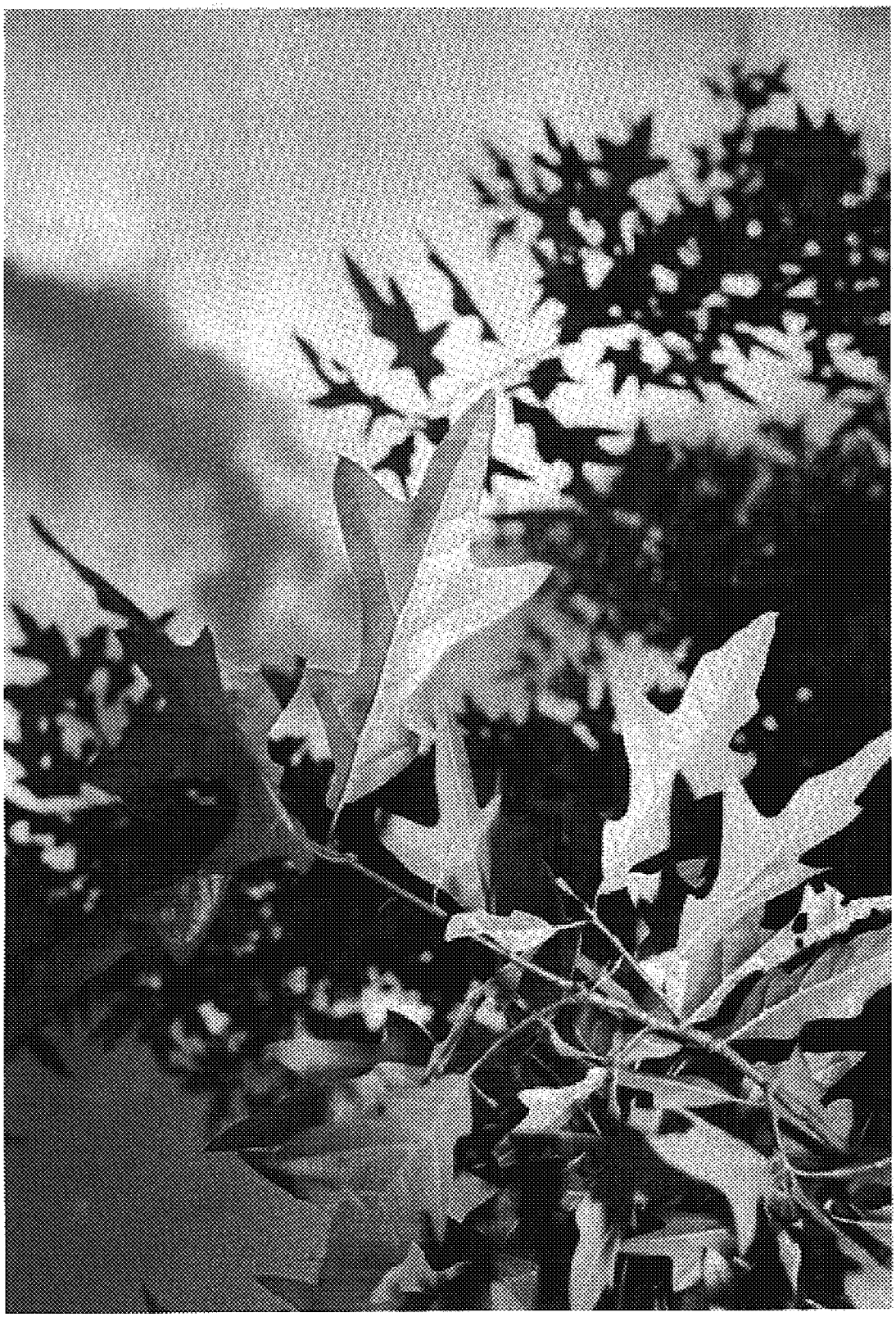
FIG. 4 is a close up of the under side of summer leaves from a tree of my new variety.
Figure 5:
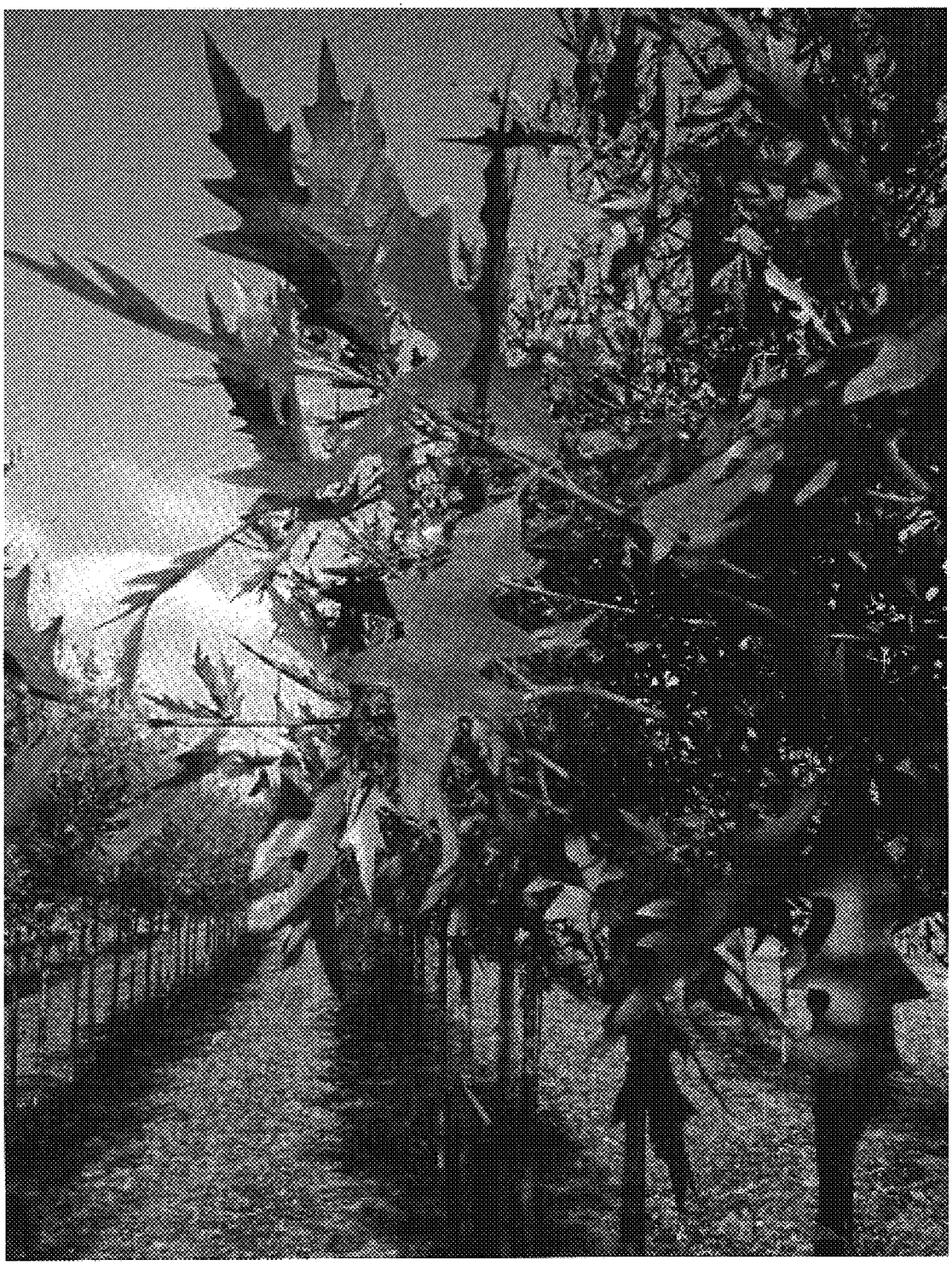
FIG. 5 is a close up of typical fall leaf color of my new variety.
Figure 6:
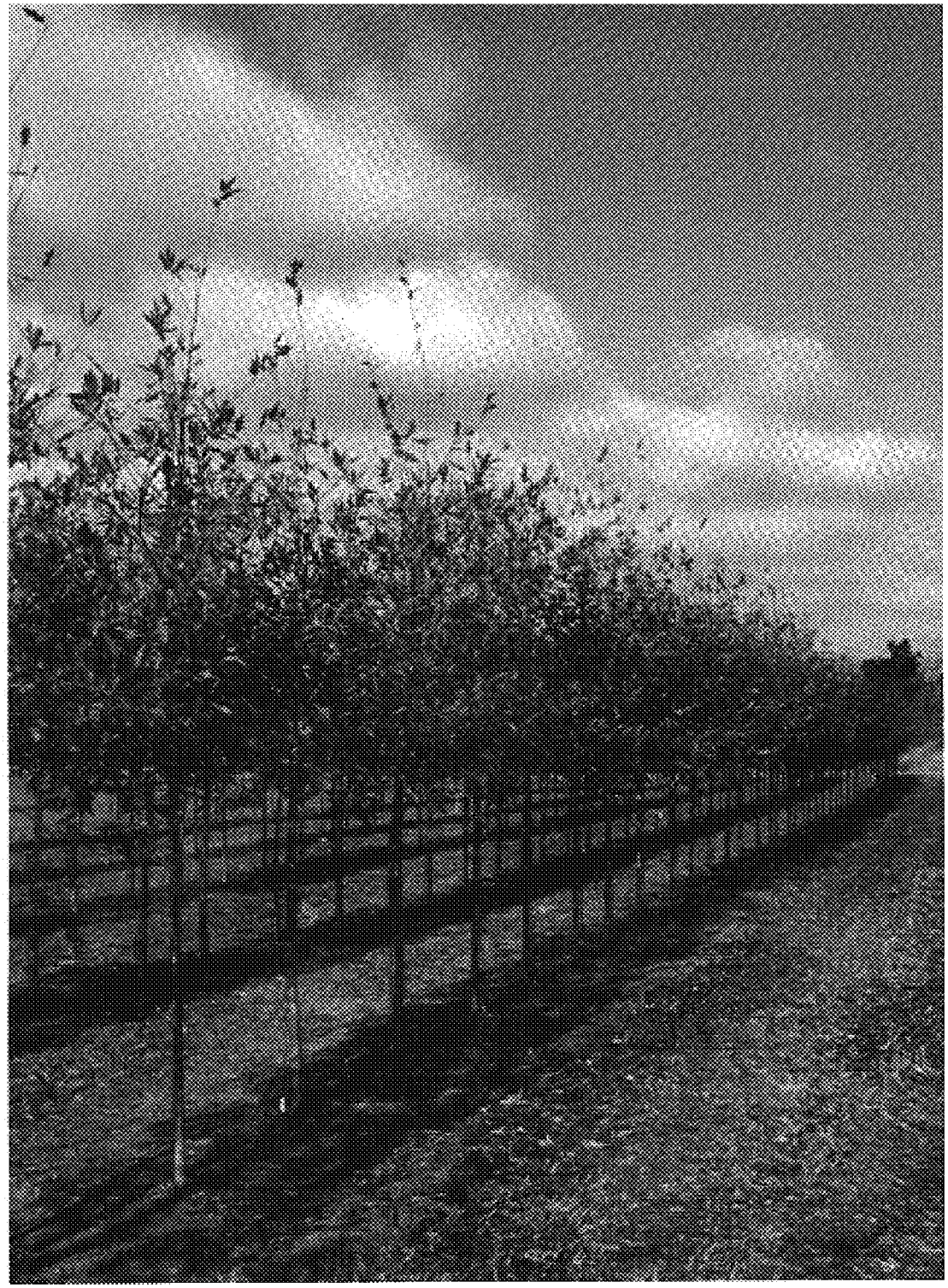
FIG. 6 is a row view of the progeny in fall color.
Figure 7:
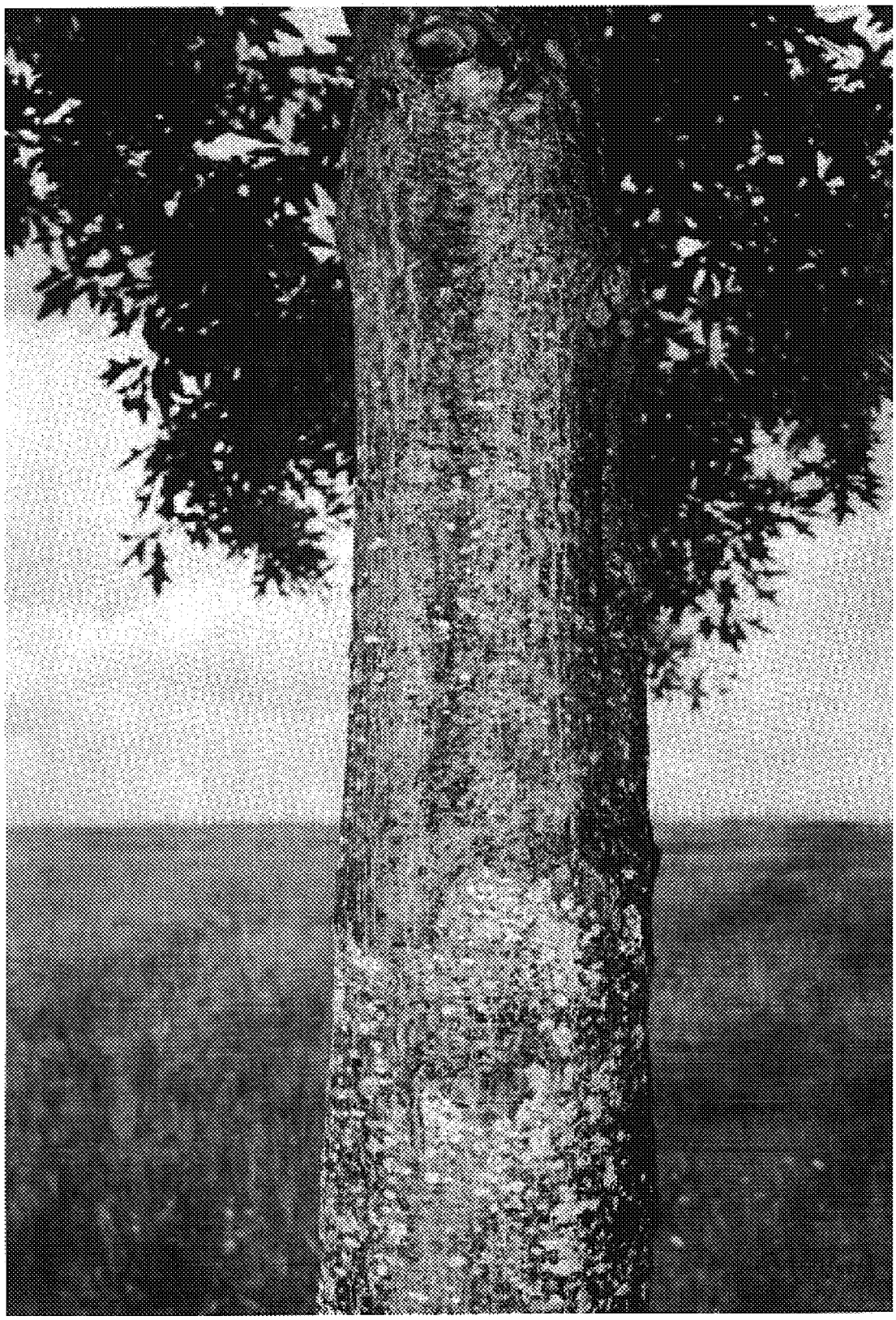
FIG. 7 is a close up of the trunk of the original tree taken at the age of nine (9) years.
Figure 8:
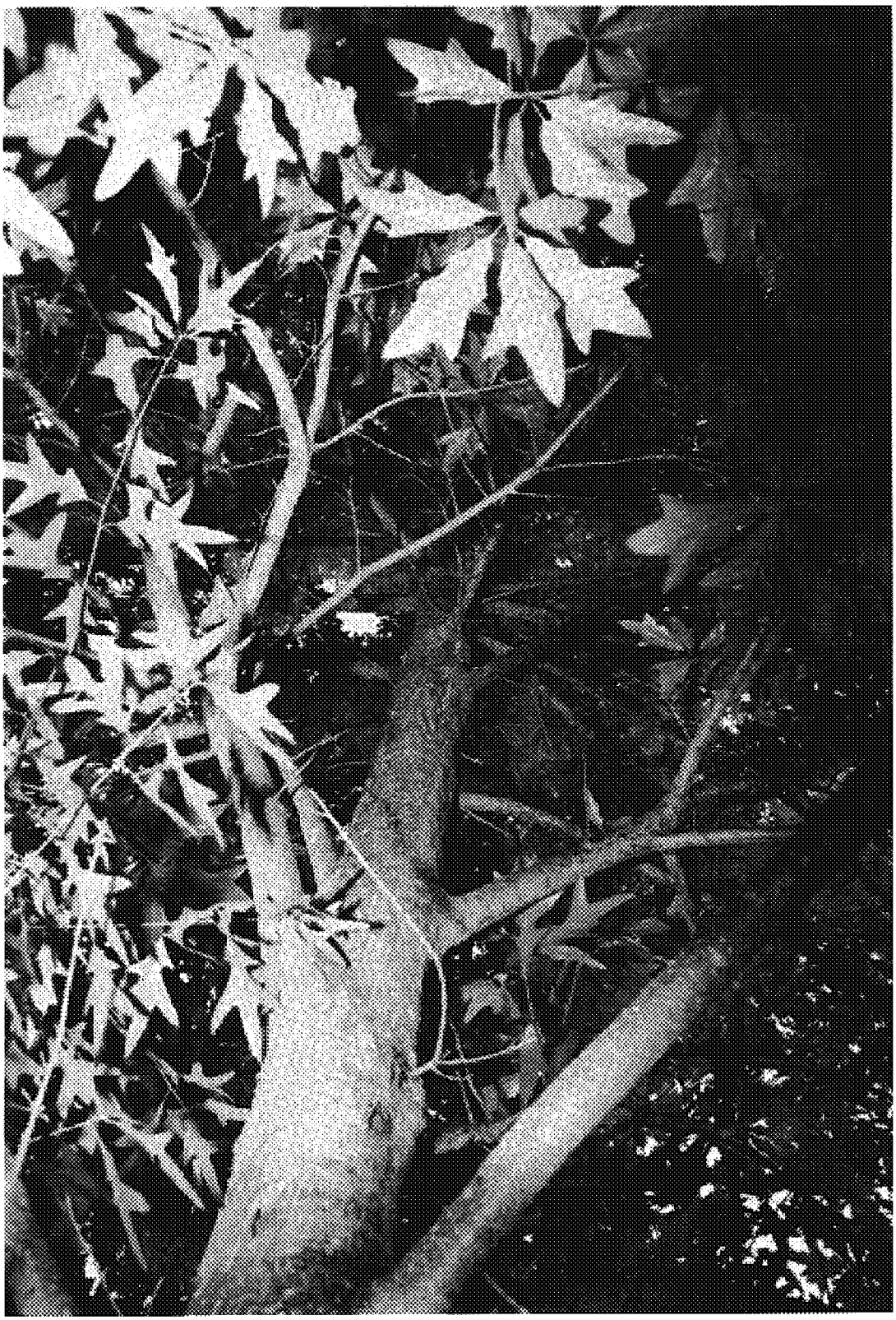
FIG. 8 is a close up of the interior branching habit of the original tree of my new variety.
Figure 9:
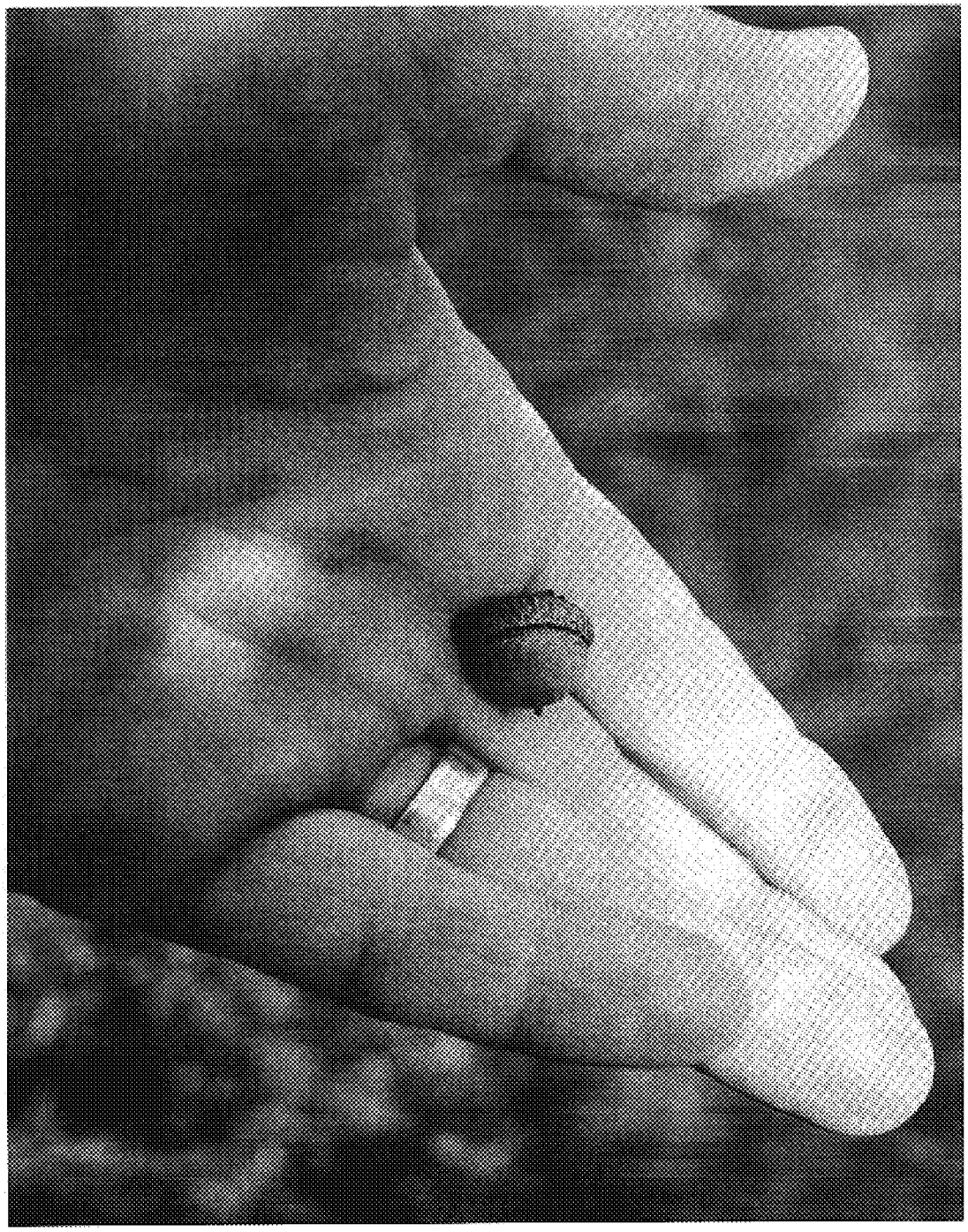
FIG. 9 is a close up of an acorn from my new variety.

The following is a detailed description of 'QXMTF' Oak with color terminology in accordance with The Royal Horticultural Society (R.H.S.) Colour Chart except where the context indicates a term having its ordinary dictionary meaning.

My new tree has not been observed under all growing conditions, and variations may occur as a result of different growing conditions. All progeny of my new variety, insofar as have been observed, have remained genetically stable in all characteristics described hereinafter.

Parentage: Seed parent is unknown.

Locality where grown and observed: 'QXMTF' Oak trees are currently in production at Loganville, Walton County, Ga. This area of Walton County has a clay loam soil type with rainfall that varies between 30" and 60" annually. This particular area is located in USDA Hardiness Zone 7.

Size and growth rate: The original tree was 8¾ inches in caliper measured at 12 inches above the ground at the age of 9 years. It had a height of 28 feet and spread of 17 feet which provides a 1.65 height to width ratio. Prior to 'QXMTF' parent tree being transplanted to the observation area, the average caliper growth rate was about 1 inch to 1.25 inches per year.

Foliage: Alternate, simple, 4 to 5 inches long and 3 to 4 inches wide. The shape is roughly obovate in outline, 5 to 7 falcate lobes with deep sinuses, bristle tips on the ends, and rounded leaf bases that are slightly offset. Summer foliage upper side of leaf is glossy smooth yellow-green like (RHS146A) while the slightly fuzzy underside is like (RHS144A) and leaf venation color is like (RHS 144B). Fall foliage upper side of leaf is bright orange like (RHSN25A) and the underside also is bright orange like (RHSN25A).

Petiole: Smooth, ¾" to 1½" long. Yellow-green like (RHS 144A).

Buds: Imbricate, ⅛" to ¼" long, ovoid, sharp-pointed, reddish brown (RHS182B).

Flowers: Monoecious, borne on staminate catkin pendants.

Fruit: From a limited amount of acorns from the original tree, the following observations can be made. The fruit resembles that of a Southern Red Oak in shape but is predominately borne solitary like that of a Shumard Oak. Acorns are nearly globular-shaped, ½ inch long and have a greyed-orange color (RHS177A). The cap covers slightly less than one-third of the nut. The cap is grayed brown (RHS199A).

Trunk: In youth, smooth, grayed-green like (RHS 198B), becoming grayed-brown like (RHS201B) and developing irregular furrows and scales with age. At the age of 9 years, the trunk diameter was 8¾" measured 12" above the ground.

Branching: Slightly ascending to nearly horizontal at the base, emerging at 50 to 60 degrees from the trunk. Upper branches are more ascending, emerging at 30 degrees or more from the trunk. Stem color on softwood is yellow green like (RHS 144A), with hardwood being grayed-green like (RHS198C).

Shape: Broad pyramidal with dense branching and dominant central leader.

Root system: Fibrous.

Vigor: In production, the progeny have averaged 1 inch to 1.25 inches of caliper per year.

Winter hardiness: Observed to be hardy in at least USDA Zone 7.

Disease: Free from disease.

Pests: Displays spider mite resistance; many oaks can develop serious mite problems that affect growth and leaf color during the summer growing season. Leaf hopper damage has been noticed.

I claim:

1. A new and distinct variety of hybrid oak tree substantially as illustrated and described herein.

* * * * *